(12) United States Patent
Alfaro Santafe et al.

(10) Patent No.: US 11,317,829 B2
(45) Date of Patent: May 3, 2022

(54) SYSTEM FOR CAPTURING A PLANTAR IMAGE

(71) Applicant: PODO ACTIVA, S.L., Cuarte (ES)

(72) Inventors: Jose Victor Alfaro Santafe, Cuarte (ES); Jose Javier Alfaro Santafe, Cuarte (ES); Angel Peguero Lorenz, Cuarte (ES); Antonio Gomez Bernal, Cuarte (ES); Carla Lanuza Cerzocimo, Cuarte (ES); Aitor Perez Morcillo, Cuarte (ES)

(73) Assignee: PODO ACTIVA, S.L., Cuarte (ES)

( * ) Notice: Subject to any disclaimer, the term of this patent is extended or adjusted under 35 U.S.C. 154(b) by 0 days.

(21) Appl. No.: 17/059,725

(22) PCT Filed: Jun. 22, 2018

(86) PCT No.: PCT/ES2018/070445
§ 371 (c)(1),
(2) Date: Nov. 30, 2020

(87) PCT Pub. No.: WO2019/243642
PCT Pub. Date: Dec. 26, 2019

(65) Prior Publication Data
US 2021/0106255 A1 Apr. 15, 2021

(51) Int. Cl.
*A61B 5/00* (2006.01)
*A61B 5/107* (2006.01)
(Continued)

(52) U.S. Cl.
CPC ............ *A61B 5/1079* (2013.01); *A43D 1/025* (2013.01); *A61B 5/1074* (2013.01); *H04N 13/204* (2018.05)

(58) Field of Classification Search
CPC .... A61B 5/1079; A61B 5/1074; A43D 1/025; H04N 13/204; H04N 13/271; G01B 11/24; G01B 5/0004
See application file for complete search history.

(56) References Cited

U.S. PATENT DOCUMENTS

2006/0283243 A1   12/2006   Peterson
2011/0313321 A1*  12/2011   Alfaro Santafe ...... A61B 5/103
                                                    600/587
(Continued)

FOREIGN PATENT DOCUMENTS

CN    107970026 A    5/2018
ES      2336533 A1   4/2010
(Continued)

OTHER PUBLICATIONS

International Search Report for Corresponding International Application No. PCT/ES2018/070445 (4 Pages) (dated Mar. 15, 2019).

*Primary Examiner* — Howard D Brown, Jr.
(74) *Attorney, Agent, or Firm* — Lucas & Mercanti, LLP (57) ABSTRACT

A system for capturing a plantar image is provided, which is based on a depth sensor or 3D image capturing device connected to a portable structure having: first legs; a first frame that holds a glass pane; and an elastic membrane on which a patient places his or her foot, making contact with the glass pane positioned there below, in the manner of a floor, to capture the plantar image by means of the depth sensor disposed beneath the glass pane. Respective platforms provided with a pair of second legs can be joined to the first frame. A system is provided that includes a transparent floor in a portable structure that allows the assembly to be transported so as to be able to capture the patient's plantar image in any desired place.

8 Claims, 6 Drawing Sheets

(51) Int. Cl.
*H04N 13/204* (2018.01)
*A43D 1/02* (2006.01)

(56) References Cited

U.S. PATENT DOCUMENTS

| | | | |
|---|---|---|---|
| 2014/0276094 A1 | 9/2014 | Lidtke | |
| 2016/0249807 A1* | 9/2016 | Mougin | A61B 5/0064 |
| | | | 600/407 |
| 2017/0228859 A1* | 8/2017 | Schouwenburg | A43B 7/1435 |
| 2017/0360298 A1* | 12/2017 | Mougin | A61B 5/0073 |

FOREIGN PATENT DOCUMENTS

| | | |
|---|---|---|
| WO | 2009095775 A1 | 8/2009 |
| WO | 2017177304 A1 | 10/2017 |
| WO | WO-2017177304 A1 * 10/2017 | ............... A61B 5/70 |

* cited by examiner

SYSTEM FOR CAPTURING A PLANTAR IMAGE

CROSS REFERENCE TO RELATED APPLICATION

This Application is a 371 of PCT/ES2018/070445 filed on Jun. 22, 2018 which is incorporated herein by reference.

OBJECT OF THE INVENTION

The following invention relates to a system for capturing the plantar image by scanning the sole of the foot, which is based on a depth sensor or 3D image capturing device connected to a portable structure comprising height-adjustable legs, a first frame that holds a glass pane, and an elastic membrane on which a patient places his or her foot, making contact with the glass pane positioned therebelow to capture the plantar image. In a practical embodiment of the invention, a pair of platforms provided with a pair of height-adjustable legs on the side thereof opposite the hinged side can be hingedly joined to two opposite sides of the first frame that holds the glass pane. Therefore, the essential subject matter of the invention is a system equipped with a portable structure with an elastic membrane to step on with the foot and a floor or stop in the form of the transparent glass pane, whereon the foot is finally supported, the system being enabled to transport the entire assembly so as to be able to capture the patient's plantar image in any desired place.

Thus, by being able to transport the entire assembly in a simple way, in many situations it can be moved to the place where it will be used without the users or patients being the ones to move to where the system is located. In this way, for example, in cases involving the manufacture of customised insoles for a group of people, such as the members of a sports team, the assembly required for capturing the plantar image can be moved without all team members having to move to where the fixed installation of the system is located.

BACKGROUND OF THE INVENTION

As is known, plantar scanners on the market normally obtain the image of the foot stepping on a glass pane, such that both the image of the heel and that of the forefoot appear flattened and the plantar arch appears significantly smaller.

Furthermore, the holder of this file is also the holder of patent document ES 2336533 which discloses a device for capturing the plantar image, which is based on a scanner by means of which a virtual image can be obtained with high precision and in an actual load situation of the patient, scanning the soft tissue and simulating the situation inside the shoe.

To do so, a structure is connected to the plantar scanner which enables it to adapt to the same, which is based on a pair of width and height-adjustable supports, which pass through it at the top by means of a pair of beams between which there is an elastic membrane on which users place their foot to be scanned.

One noteworthy fact is that moving the plantar scanners, both due to the volume and possible misalignment thereof, represents a significant drawback.

DESCRIPTION OF THE INVENTION

A system for capturing a plantar image is described in the present specification, which comprises:

a depth sensor or 3D image capturing device, and,
a portable structure defined by:
  adjustable legs each made up of a tubular central body that houses, at each end respectively, a first body and a second body, both height-adjustable inside the tubular central body;
  a first frame that holds a glass pane, joined to the tubular central body of each adjustable leg, and;
  an elastic membrane, joined to the second body of the first legs.

The first frame that holds the glass pane, which acts in the manner of a transparent floor or stop, is joined to the tubular central bodies that make up the first legs, being height-adjustable by means of adjusting the first bodies that make up the adjustable legs, which are supported on the floor by support bases.

In a first embodiment, the elastic membrane is located in a second frame which, in turn, is joined to the second bodies that make up the first legs.

In a second embodiment, the elastic membrane is fixed to a pair of parallel crossbars which, in turn, are fixed to the second bodies that make up the first legs, such that the tension of the membrane can be adjusted by anchoring means located on the pair of crossbars.

In both embodiments, the elastic membrane is height-adjustable with respect to the first frame through the position-adjusting capacity of the second body along the tubular central body.

In either of the two embodiments of the invention, a pair of platforms provided with corresponding pairs of pivotably joined, height-adjustable second legs on the side thereof opposite the hinged side are hingedly joined to the respective platform by means of rotation axes on two opposite sides of the first frame.

Each second leg houses at the free end thereof a third body for adjusting height.

Both the first bodies, which make up the first legs of the portable structure, and the third bodies, which make up the second legs, pivotably joined to the platforms, terminate in respective rotating support bases by means of rotation axes.

Therefore, since both the first legs and the second legs terminate in respective rotating support bases, based on the height adjustment of the assembly of legs and the pivoting of the support bases thereof, the overall structure is able to be tilted up to 45° with the aim of making it easier to scan the foot in different positions.

BRIEF DESCRIPTION OF THE FIGURES

To complement the following description and for the purpose of helping to better understand the features of the invention, a set of drawings is attached to the present specification, in the figures of which, by illustration and not limitation, the most characteristic details of the invention are represented.

FIG. 5 shows a perspective view of the system of the invention in a second embodiment wherein a pair of crossbars that hold the elastic membrane are fixed to the second bodies that make up the first legs of the portable structure, also showing platforms hingedly joined to the first frame on two of the sides thereof and having respective pairs of rotatably joined, height-adjustable legs on the side opposite the hinged side, while.

A list of the references used in the figures is provided below:
1. Depth sensor.
2. First portable structure.
2'. Second portable structure.
3. First frame.
4. First legs.
5. Tubular central body.
6. First body.
7. Second body.
8. Glass pane.
9. Second frame.
10. Elastic membrane
11. Crossbar.
12. Platform.
13. Second legs.
14. Rotation axis.
15. Third body.
16. Support base.

DESCRIPTION OF A PREFERRED EMBODIMENT

In view of the aforementioned figures and according to the adopted numbering, it can be observed how the system for capturing a plantar image of the present invention mainly comprises a depth sensor 1 and a portable structure 2, 2', the depth sensor 1 being able to be defined by a mobile device capable of capturing 3D images in real time, such as a laptop PC with a webcam, a mobile phone, a tablet or any electronic device equipped with a depth sensor 1.

Figure 1:
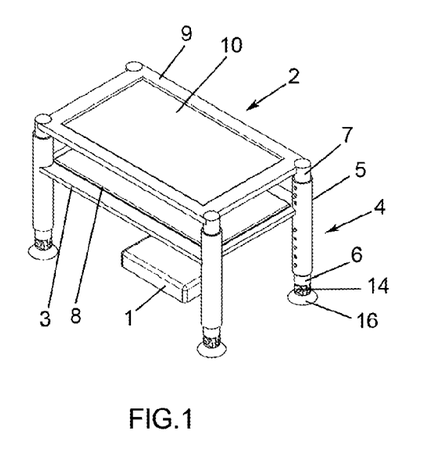
FIG. 1 shows a perspective view of the system of the invention in a first embodiment with a sensor under the same in correspondence with the glass pane of the first frame and the elastic membrane of the second frame.
Figure 2:
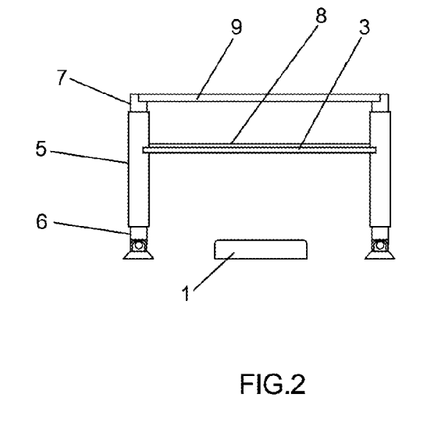
FIG. 2 shows a first side elevation view of the preceding figure, showing how the sensor is centred under the portable structure.
Figure 3:
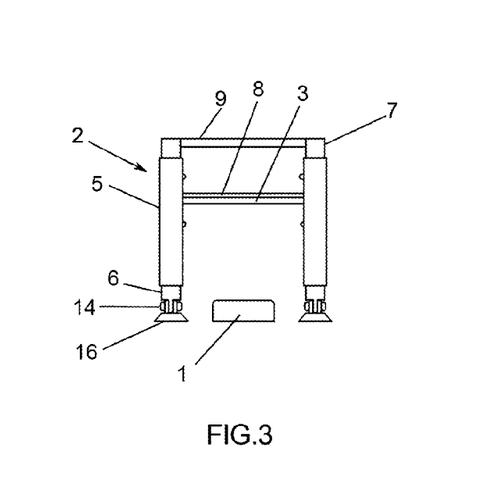
FIG. 3 shows a second side elevation view of FIG. 1, showing how the sensor is centred under the portable structure.
Figure 4:
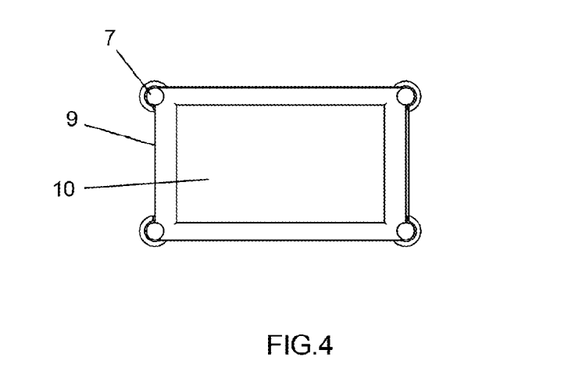
FIG. 4 shows a plan view of FIG. 1, showing the second frame with the elastic membrane.

Thus, in a first embodiment, FIG. 1 represents a first portable structure 2 comprising first legs 4 made up of a tubular central body 5 wherein a first body 6 and a second body 7 are housed at the bottom and at the top at each end, being adjustable in position with respect to the tubular central body 5. The first portable structure 2 also comprises a first frame 3 that holds a glass pane 8, joined to the tubular central body 5 that makes up the respective first legs 4, and a second frame 9 that holds an elastic membrane 10, located above the first frame 3.

With this configuration, it has an elastic membrane 10 for capturing the plantar image of a foot when placed on it and a transparent floor or stop by means of the glass pane 8 of the first frame 3, whereon the foot ends up being supporting in order to proceed with scanning by using the depth sensor 1 or equivalent mobile device, disposed under the glass pane 8.

Moreover, the height of the first legs 4 is adjusted by positioning the first body 6 and the second body 7 with respect to the tubular central body 5.

Therefore, the position of the first frame 3 that holds the glass pane 8 is height-adjustable by means of adjusting the first body 6 with respect to the tubular central body 5.

Furthermore, the distance between the second frame 9 that holds an elastic membrane 10 and the first frame 3 that holds the glass pane 8 is adjustable by means of the second body 7 along the tubular central body 5 that makes up the first legs 4.

Therefore, to capture the plantar image of the patient or user, a lateral support, not represented in the figures, is attached to the first portable structure 2, so that the patient or user can place his or her foot that is not being used to obtain the plantar image on the same, being able to adopt a stable and comfortable position.

Figure 5:
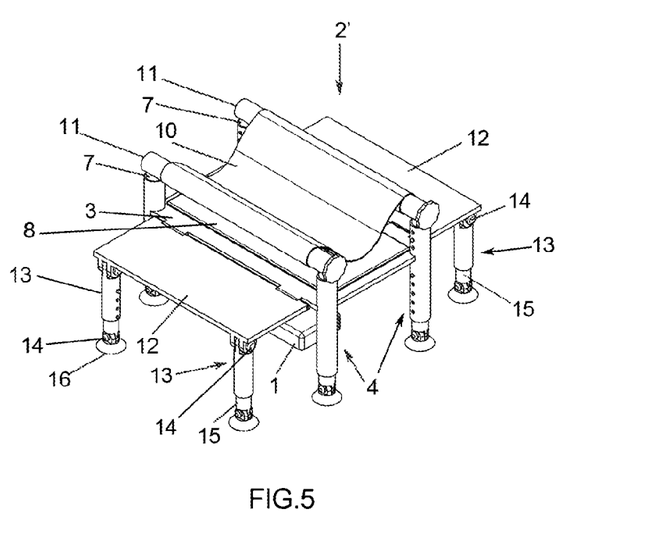
Figure 6:
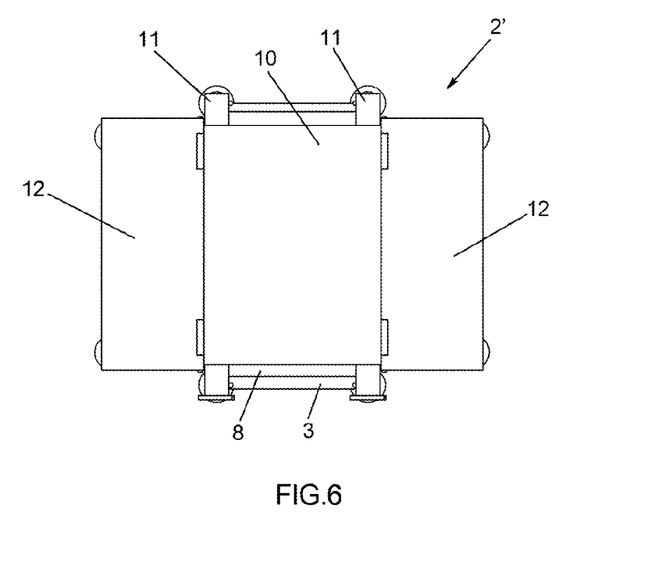
FIG. 6 shows a plan view of the preceding figure.

In a second embodiment, as represented in FIG. 5, a second portable structure 2' comprises a pair of parallel crossbars 11, fixed to the second bodies 7 of the first legs 4. The elastic membrane 10, joined by fixing means, the tension of which is adjusted by rotating the crossbars 11, is arranged between the crossbars 11.

In either of the two embodiments, either with the elastic membrane 10 supported by the second frame 9 or by the crossbars 11, respective platforms 12 which, on the sides opposite the hinged sides, have respective pairs of second legs 13 rotatably joined to the respective platforms 12 by rotation axes 14, are hinged to two of the opposite lateral sides of the first frame 3 along some sides thereof.

Said second legs 13 are height-adjustable by means of third bodies 16 that are housed therein at the desired length, in the same way as the first bodies 6 in the tubular central bodies 5 of the first legs 4.

Figure 7:
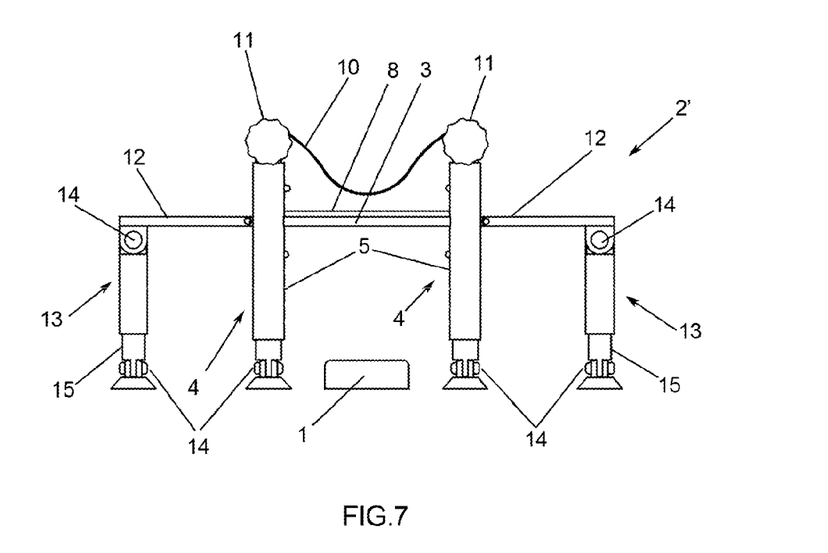
FIG. 7 shows a side elevation view of FIG. 5, showing how the pair of platforms hinged to the first frame that holds a glass pane are flush with it and allow the user to position himself or herself on them.
Figure 8:
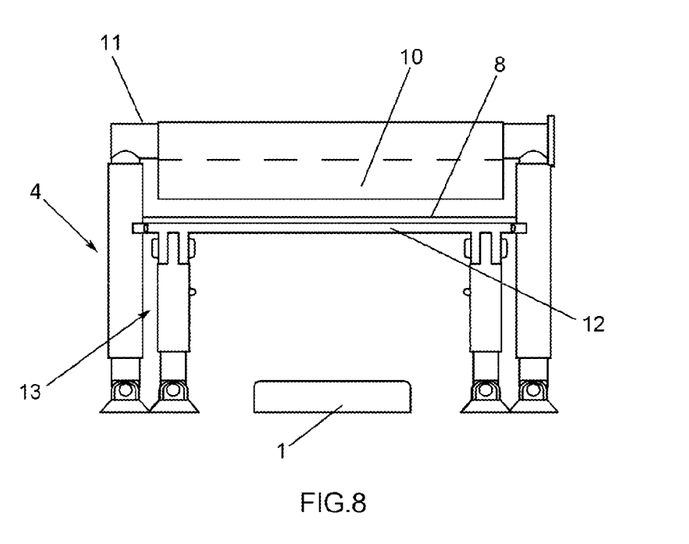
FIG. 8 shows a front elevation view of FIG. 5.

Therefore, in FIGS. 5 and 7 it can be observed how the pair of platforms 12 is flush with the first frame 3 at the same time that the pair of crossbars 11, between which the elastic membrane 10 is disposed, is fixed to the second bodies 7, such that the height of said elastic membrane 10, with respect to the glass pane 8 integral to the first frame 3, can be adjusted by means of the height adjustment of the second bodies 7 or through the fixing means for fixing said elastic membrane 10 to the pair of crossbars 11 between which it is assembled.

Figure 9:
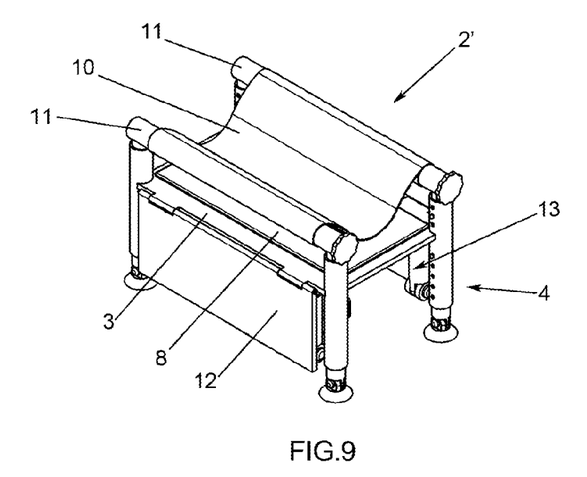
FIG. 9 shows a perspective view of the system of the invention represented in FIG. 5 in the folded position thereof.
Figure 10:
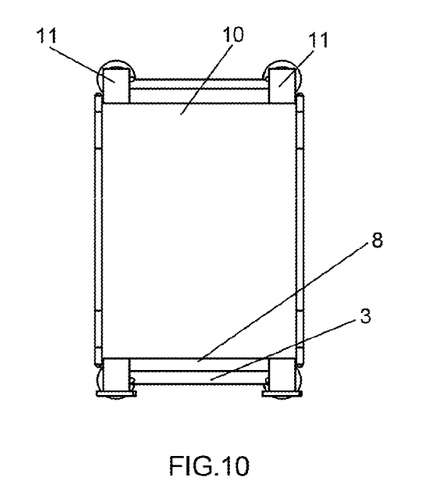
FIG. 10 shows a plan view of FIG. 9.
Figure 11:
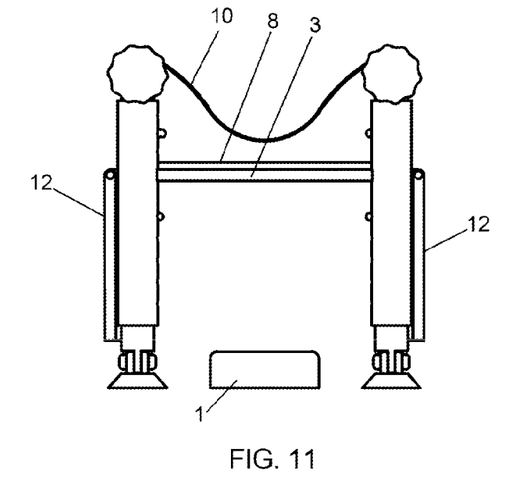
FIG. 11 shows a side elevation view of FIG. 9, showing how the pair of platforms hinged to the first frame are pivoted and with the pair of legs joined rotatably, likewise, folded on said platforms.
Figure 12:
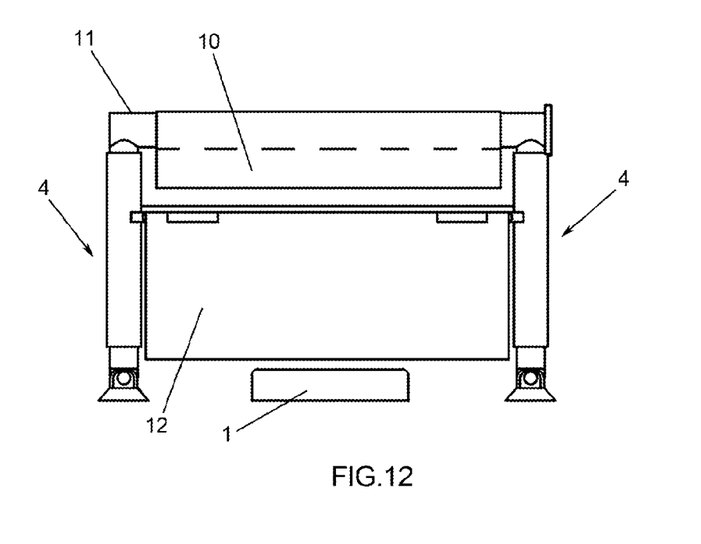
FIG. 12 shows a front elevation view of FIG. 9.

Thus, the first frame 3, with the incorporated glass pane 8, is integral to the tubular central bodies 5 that make up, together with the first bodies 6 and the second bodies 7, the first legs 4 of the first portable structure 2. This configuration defines the base support of the second portable structure 2', since the second legs 13 can pivot on the inner face of the platforms 12 and in turn the platforms 12 can likewise pivot with respect to the joint axis thereof hinged to the first frame 3, configuring the second portable structure 2' by simply adding the crossbars 11 with the elastic membrane 10 to it, as shown in FIG. 9, occupying a minimum space that facilitates the transport thereof since it folds easily.

Furthermore, by having the first bodies 6 that make up the first legs 4 connected to the first frame 3 that holds the glass pane 8, as well as the third bodies 15 that make up the second legs 13 rotatably joined to the pair of platforms 12 along the side opposite that of its hinge to the first frame 3, as indicated, the height of the assembly of the second portable structure 2' can be adjusted to the desired height when in the deployed working position thereof.

With the second portable structure 2' in the deployed working position thereof, as shown in FIG. 5, the patient can place himself or herself on it, placing the foot to be scanned on the elastic membrane 10 until making contact with the glass pane 8, in the manner of a transparent floor or stop, and scanning the foot by means of the depth sensor 1 or equivalent mobile device arranged therebelow, while the other foot will be supported on one of the platforms 12 and, when said scan has been completed, the patient or user will only have to change the position of the feet so that they will place the already scanned foot on the free platform 12 and the other foot, placed on the platform 12, will be placed on the membrane 10, stepping on it to make contact with the glass pane 8, in the manner of a transparent floor or stop, to proceed with the scanning thereof.

Furthermore, both the first legs 4 and the second legs 13, rotatably joined to the pair of platforms 12, terminate therebelow with respective support bases 16 rotatably joined by corresponding rotation axes 14, allowing the rotation of the structure up to 45° and making it easier to scan the feet at a certain angle.

Therefore, when the circumstances require a change in the location of the scan site, the second structure 2' will be able to fold and be moved to the scan site, together with the suitable depth sensor 1 which, as indicated, can be defined by a portable PC or similar means, and the plantar image is captured where desired given the ease of transport.

The height of the first bodies 6 and of the second bodies 7, which make up the first legs 4, and of the third bodies 15, which make up the second legs 13, can be adjusted by means known in the state of the art such as, for example, by means of a series of holes coinciding with corresponding holes in the tubular central body 5 and respective elements fitted therein or by any other equivalent means.

The invention claimed is:

1. A system for capturing a plantar image, comprising:
   a device to be selected between a depth sensor and a 3D image capturing device, and;
   a portable structure defined by:
      a plurality of first legs, each leg of the plurality of first legs comprising a tubular central body having a top end and a bottom end, a first body housed at the bottom end and a second body housed at the top end;
      a first frame that holds a glass pane, joined to the tubular central body of the plurality of first legs, and
      an elastic membrane, joined to the second body of the plurality of first legs,
   wherein:
      the position of both the first body and the second body with respect to the tubular central body is adjustable, and
      a foot of which the plantar image is to be obtained is positioned on the elastic membrane until it is supported on the glass pane of the first frame to be scanned.

2. The system for capturing a plantar image, according to claim 1, wherein the elastic membrane is fixed in a second frame that is fixed to the second bodies of the first legs, the distance to the first frame being adjustable.

3. The system for capturing a plantar image, according to claim 1, wherein the elastic membrane is fixed to a pair of parallel crossbars, fixed to the second bodies of the first legs and with the ability to rotate to adjust the tension of the elastic membrane, the distance to the first frame being adjustable.

4. The system for capturing a plantar image, according to claim 2, wherein the assembly formed by the elastic membrane and the first frame is height-adjustable by means of adjusting the first bodies with respect to the tubular central body that makes up the first legs.

5. The system for capturing a plantar image, according to claim 2, wherein the elastic membrane is height-adjustable with respect to the first frame by means of adjusting the second bodies with respect to the tubular central body that makes up the first legs.

6. The system for capturing a plantar image, according to claim 2, further comprising a pair of platforms hingedly joined to two opposite sides of the first frame, wherein each platform in turn comprises, on the side opposite the hinged side, a pair of second legs pivotably joined by means of rotation axes to the corresponding platform.

7. The system for capturing a plantar image, according to claim 6, wherein the second legs comprise a third body housed therein with the ability to be adjusted, so that the second legs are height-adjustable.

8. The system for capturing a plantar image, according to claim 7, wherein both the first bodies and the third bodies have respective rotatably joined support bases by means of rotation axes.

* * * * *